United States Patent [19]

Kawasaki et al.

[11] Patent Number: 5,347,364
[45] Date of Patent: Sep. 13, 1994

[54] TOTAL REFLECTION MEASURING APPARATUS

[75] Inventors: Kazuhiko Kawasaki; Tadashi Miyazaki, both of Hachioji, Japan

[73] Assignee: Jasco Corporation, Hachioji, Japan

[21] Appl. No.: 6,770

[22] Filed: Jan. 21, 1993

[30] Foreign Application Priority Data

Jan. 23, 1992 [JP] Japan .................. 4-032778

[51] Int. Cl.$^5$ .................. G01J 3/02; G01N 21/01
[52] U.S. Cl. .................. 356/445; 250/341.1; 359/859
[58] Field of Search ............ 359/366, 391, 857, 858, 359/859, 861; 356/72, 244, 445; 250/341

[56] References Cited

U.S. PATENT DOCUMENTS 5,093,580 3/1992 Sting .................. 356/445
5,200,609 4/1993 Sting et al. .................. 356/244
5,229,611 7/1993 Ukon .................. 356/346

*Primary Examiner*—Edward K. Look
*Assistant Examiner*—James A. Larson
*Attorney, Agent, or Firm*—Ronald R. Snider

[57] ABSTRACT

A total reflection measuring apparatus having a cassegrain mirror which has cassegrain primary mirror and cassegrain secondary mirror focuses the light which is reflected by the above secondary mirror and the primary mirror on an object of measurement. A prism which is positioned in lower part of the above cassegrain secondary mirror and a prism lift which moves the prism between a shadow behind the cassegrain secondary mirror and the object. The prism lift positions the prism in the shadow behind the cassegrain secondary mirror when visual observation is required. As a result, the clear observation of object becomes possible.

4 Claims, 4 Drawing Sheets

TOTAL REFLECTION MEASURING APPARATUS

FIELD OF THE INVENTION

The present invention relates to a total reflection measuring apparatus and more particularly, to the improvement of the total reflection measuring apparatus for micro measurement.

BACKGROUND ART

Generally, an object is measured by using a microscope. For example, it becomes possible to analyze portions of a part from an infrared spectrum of the part measured by using the microscope.

To obtain the optical data from the object, it is necessary to gather a reflected light from the object or a transmitted light by the object.

However, it is very difficult to apply a prior art technique to gather the reflected light or the transmitted light of the object when the object of measurement is such as a surface of macromolecule film or semiconductor, or materials which strongly absorb light such as an aqueous solution which absorbs the infrared light.

From this reason, a total reflection measuring method is applied to an object where it is difficult to measure the reflected light or the transmitted light from the object.

The principle of the total reflection measuring method is explained with reference to FIGS. 5A and 5B.

An ATR hemisphere prism 12 or ATR triangle pole prism 12 having a refractive index bigger than that of the object 10 is placed on the object 10, and a beam of light having a wavelength $\lambda$ is entered into the prism 12.

When the angle of incidence from the prism 12 to the object 10 is bigger than the critical angle, the light is totally reflected at the critical surface between the object 10 and the prism 12. At this reflection point, the beam of light enters the sample a little. The entering depth $d_p$ is represented by the following formula (1):

$$d_p = \lambda / [2\pi n_1 \{\sin^2\theta - (n_2/n_1)^2\}^{\frac{1}{2}}] \quad (1)$$

wherein $d_p$ represents an entering depth that the light strength decreasing to i/e, and $\lambda$ represents the wavelength of the light.

Therefore, the totally reflected light decreases according to the absorption of the light at the critical surface. As a result, it becomes possible to obtain optical information from the object of measurement by analyzing characteristics of the total reflection light at the critical surface between the object and the prism, even if the object is a surface such as a macromolecule film or a semiconductor, or materials which strongly absorb the light.

However, when applying a conventional total reflection measuring apparatus to the general micro measuring apparatus, it is necessary to observe the measured part of the object by visual observation in visible light. The object has to be placed on a total reflection measuring apparatus, the total reflection measuring apparatus has to be connected to the micro measuring apparatus to obtain the optical information. As mentioned above, it required a very complex operation. Further, the improvement of the measurement precision was limited.

DISCLOSURE OF THE INVENTION

Accordingly, it is an object of the present invention to eliminate the above-described problems of the prior art and to provide a total reflection measuring apparatus which can efficiently obtain optical data by total reflection measurement from small portions of the object of measurement.

The total reflection measuring apparatus according to the present invention includes a cassegrain mirror, a prism and a prism lifting means to achieve the above purpose.

The cassegrain mirror has a primary mirror and a secondary mirror, focuses the light which is reflected by the secondary mirror and the primary mirror on the object to be measured, and reflects light by the primary mirror and the secondary mirror.

Also, the prism is positioned between the casssegrain secondary mirror and the object of measurement.

The prism lifting means makes the prism shiftable between the surface of the object of measurement and a shadow part under the cassegrain secondary mirror.

Since the total reflection measuring apparatus according to the present invention includes the above-mentioned means, when selecting the measuring part of the object, the prism is lifted to the shadow part behind the cassegrain secondary mirror by the prism lifting means. Therefore, the incident light from the cassegrain mirror is irradiated on the object without transmitting through the prism, and the reflected light from the object is also obtained from the object without transmitting through the prism. As a result, it becomes possible to confirm the measuring part of the object by visual observation.

On the other hand, when measuring a total reflection of the object, the above prism lifting means makes the prism move down and come in contact with the surface of the object. And then, it becomes possible to measure the total reflection because the irradiated light from the cassegrain mirror is totally reflected at the boundary between the prism and the surface of the object.

As described above, the total reflection measuring apparatus according to the present invention makes it possible to observe the object directly when selecting the measuring part of the object. As a result, the selecting procedure of the measuring part is very easy.

Said prism lifting means is preferably provided with a cylinder, a moving shaft which is inserted in the cylinder so as to be movable in the cylinder, a prism holding board which is fixed on the bottom of the moving shaft, and a spring which pulls the moving shaft toward the cassegrain second mirror.

Furthermore, said prism lifting means is preferably provided with a stopper ring which can position the prism so as to contact to the object.

DESCRIPTION OF THE PREFERRED EMBODIMENTS

The preferred embodiments of the present invention will be described in detail with reference to the accompanying drawings.

Figure 1:
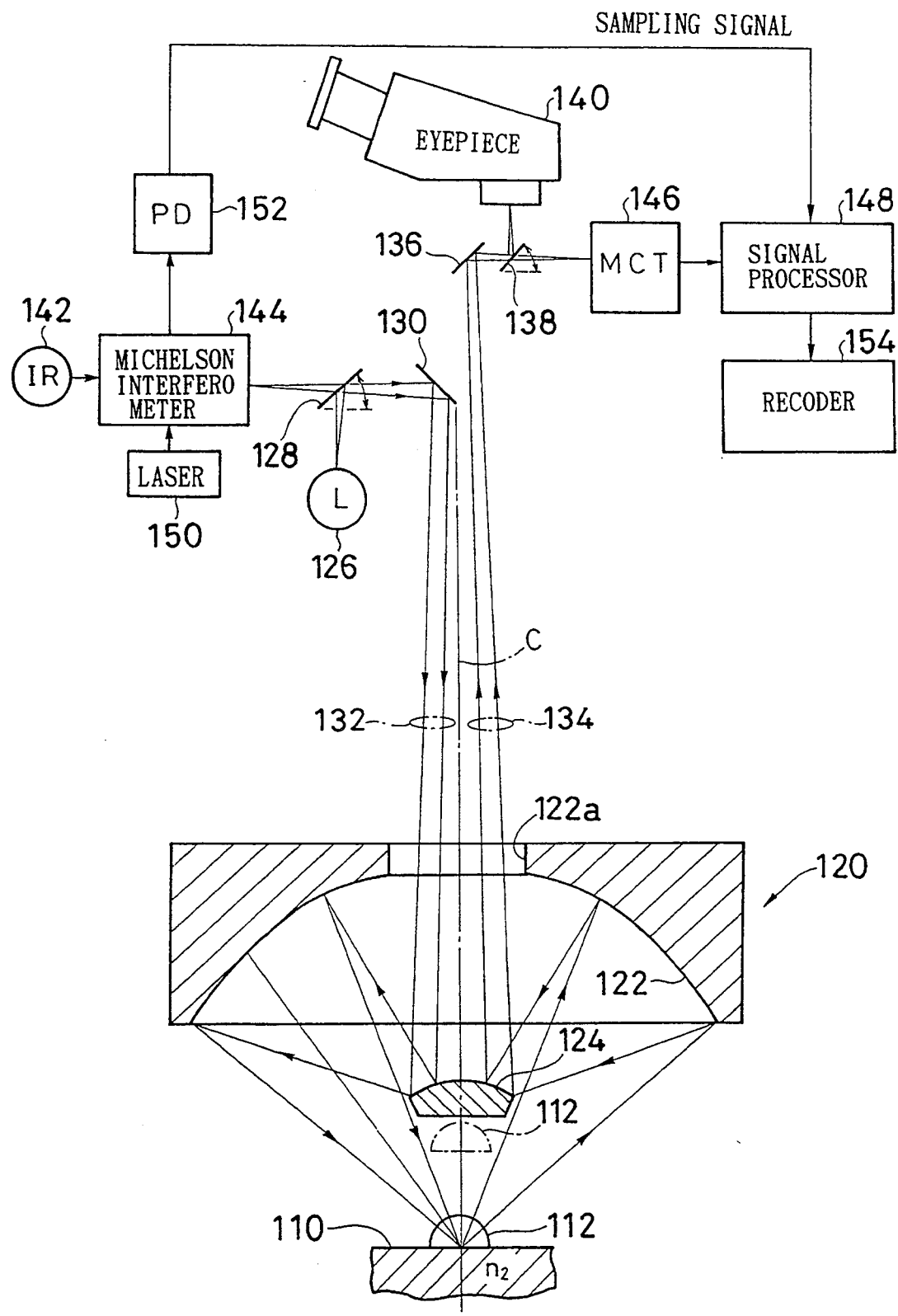
FIG. 1 is a schematic explanatory view of the total reflection measuring apparatus according to the present invention.
Figure 5A:
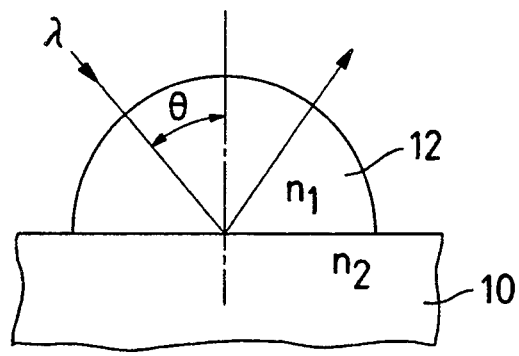
FIGS. 5A and 5B are an explanatory view of the principle of total reflection measuring.
Figure 5B:
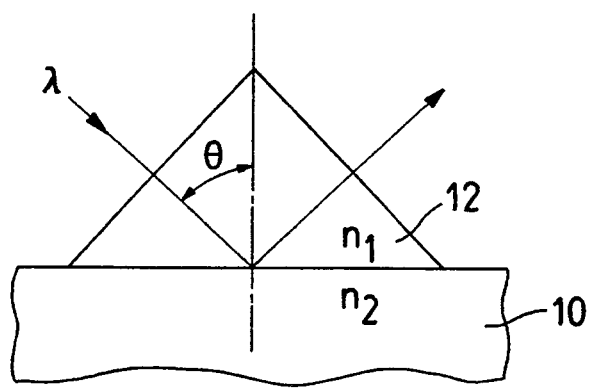

FIG. 1 is an explanatory view of the total reflection measuring apparatus according to the present invention. The same numerals prefixed by the numeral 1 are provided for the elements which are the same for those in FIGS. 5A and 5B, and explanation thereof will be omitted.

The total reflection measuring microscope which is shown in the figure is composed of a cassegrain mirror 120 and a prism 112 having hemisphere shape.

The cassegrain mirror 120 includes a cassegrain primary mirror 122 and cassegrain secondary mirror 124. The cassegrain primary mirror 122 comprises a concave mirror having hole 122a at a center thereof. The cassegrain secondary mirror 124 comprises a convex mirror with the diameter which is smaller than that of the cassegrain primary mirror 122. The central axis C of the cassegrain primary mirror 122 corresponds to that of the cassegrain secondary mirror 124.

The prism 112 has almost semi-spherical shape and the convex portion of the prism opposite to the cassegrain primary mirror 122. The central axis of prism 112 corresponds to the central axis C of the cassegrain mirror 120. The central point of the prism 112 is arranged to be able to correspond to the light focus position of the cassegrain mirror 120.

When observing a portion of the object 110 to be measured by visual observation, the prism 112 is lifted as shown in alternate long and short dash lines in the figure. The beam of light irradiated from a visible light source 126 is reflected by a shiftable mirror 128 which is shiftable in/out the optical path and a fixed mirror 130, and forms incident light 132. And then, the incident light 132 is directly focused on the object of measurement 110 through the cassegrain secondary mirror 124 and the cassegrain primary mirror 122. The reflected light from the object 110 is reflected by the cassegrain primary mirror 122 and the cassegrain secondary mirror 124, and becomes an outgoing beam 134. The outgoing beam 134 is led to an eyepiece 140 by being reflected with a fixed mirror 136 and shiftable mirror 138 which is shiftable in/out the optical path.

When measuring a total reflection spectrum, as shown by the solid line in the figure, the prism 112 is lowered. The shiftable mirrors 128 and 138 are shifted from the light path to out. The beam of the light irradiated from the infrared light source 142 is led to the Michelson interferometer 144 and generates an infrared interference light. The outgoing beam 134 is reflected by the fixed mirror 136 and the strength of the beam 134 is measured by the MCT detector 146. The detected signal is supplied to the signal processor 148. On the other hand, the leaser light irradiated from the laser 150 is led to the Michelson interferometer 144 and generates an interference laser. The strength of the interference laser is detected by the photodiode 152 and the detected signal is supplied to the signal processor 148 as a sampling signal. The signal processor 148 reads the light strength signal from the MCT detector 146 synchronizing with the sampling signal. And then, the signal processor 148 processes the signal by a known method and forms an infrared absorption spectrum and memorizes it in a recorder 154.

The characteristic point of the present invention is, when observing the measuring portion of the object by visual observation, the prism 112 is lifted to the shadow part under the cassegrain secondary mirror 124. Therefore, the apparatus according to the example provides the prism lifting means 160 as shown in FIG. 2 and FIG. 3.

The prism lifting means 160 is comprised of three cylinders 162 (only one cylinder is shown in the figure and the others have same structure), the moving shaft 164 which is inserted in the cylinder 162 so as to be movable in the cylinder 162, and the prism holding board 166 which is fixed on the bottom tip of the moving shaft 164.

The moving shaft 164 is hollow. A spring 168 is inserted in this hollow and holds the moving shaft 164 at the upper side as shown in the figure.

Figure 2:
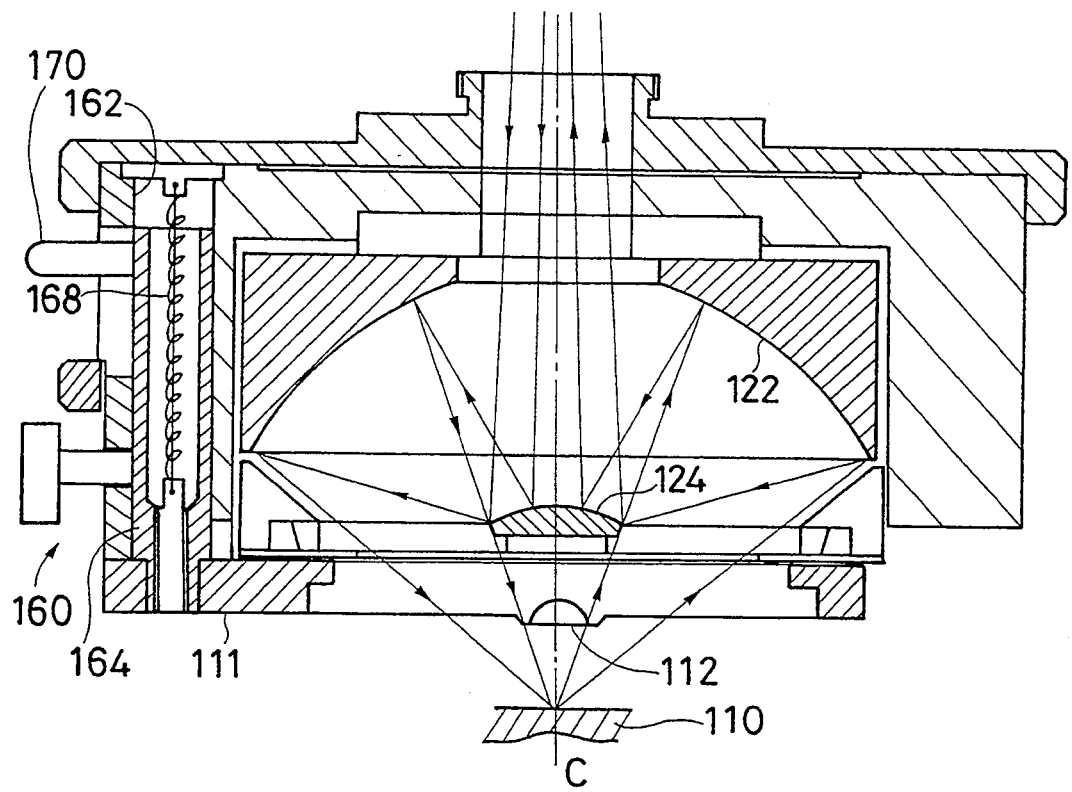
FIG. 2 and FIG. 3 are explanatory views of the prism lifting means of the total reflection measuring apparatus which is shown in FIG. 1.
Figure 3:
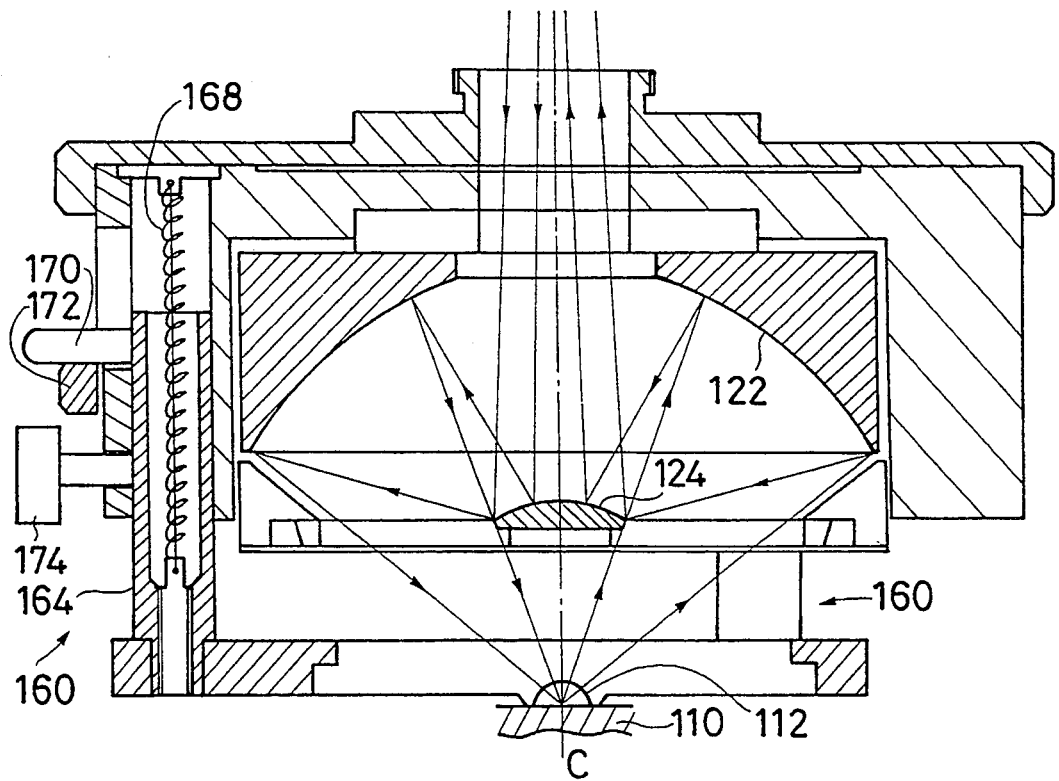

As a result, the prism holding board 166 is positioned above as shown in FIG. 2 in the visual observing condition. The prism 112 which is provided on the prism holding board 166 positioned under or behind the cassegrain secondary mirror 124 and behind the part where the shadow of the cassegrain secondary mirror 124 is.

Therefore, in the condition which is shown in FIG. 2, the structure becomes the same as a typical reflection measurement of the object 110. The object 110 is set on the XYZ stage and can be moved in each axis direction. The measuring portion can be selected by visual observation through the eyepiece 140. In this manner, it is possible to observe the surface of the object 110 directly as a microscope observation. As a result, a very clear image of the object can be observed.

On the other hand, a total reflection measuring condition with the apparatus according to the example is shown in FIG. 3.

An operation lever 170 which is fixed on the moving shaft 164 is pushed down to where the lever 170 comes in contact with a stopper ring 172. The stopper ring 172 is adjusted at the position where the focus point of the cassegrain mirror 120 corresponds to the central position of the hemisphere prism 112. And then, the prism 112 goes down according to the down of the moving shaft 164 and the prism holding board 116, the flat surface of the prism 112 comes in contact with the object 110. In this condition, the moving shaft 164 is fixed with a fixation screw 174 and the apparatus measures the total reflection.

After the total reflection measurement is finished, the fixation screw 174 is loosened. As a result, the prism 112 can be lifted up according to the moving shaft 164 and the prism holding board 116 by the tension of the spring 168 and then, it becomes the condition as shown in FIG. 2.

As mentioned above, according to the total reflection measuring microscope of the present example, when the visual observation of the object of measurement is required, the prism 112 is positioned in the part of the shadow of the cassegrain secondary mirror 124. As a result, it is possible to observe the object directly and to select a total reflection measuring part by observing the clear enlarged image of the object. Also, when a total reflection is to be measured, the prism 112 goes down just as it is. And then, the prism 112 comes in contact with the measuring part of the object 110. As a result, the subtle and complicated adjusting of the prism position is not necessary, and it is possible to measure the total reflection very easily.

Incidentally, it is necessary to adjust the top position and the bottom position of the stopper ring 172 according to change of the prism 112.

In this case, the operation lever 170 is pushed down like the condition of the reflection measurement by the cassegrain mirror 120 in the condition of the object is not mounted. The stopper ring 172 is operated so as to go up and down where the central position of the hemisphere prism 112 corresponds to the focus position of the cassegrain mirror 120. Incidentally, if fixation between the stopper ring 172 and a body is made as screw like, it is possible to control the position of the stopper ring 172 by turning itself.

On the other hand, the prism 112 is positioned where the central position of the hemisphere thereof corresponds to the focus position of the cassegrain mirror 120. It is possible to adjust the central position of the prism by observing the output of the reflected light which is obtained from the infrared light through the cassegrain mirror 120 and the prism 112, and being reflected at the base of the prism 112 and coming out again through the prism 112.

As mentioned above, in cases where the central position of the prism 112 corresponds to the focus position of the cassegrain mirror 120, the output of the detector 146 becomes maximum. Therefore, it is possible to adjust easily the position of the stopper ring 172.

In addition to the total reflection light from the boundary between the prism 112 and the object 110, the reflected light from the prism 112 sometimes includes a reflected light from the object 110.

The critical angle $\theta_c$ generates total reflection. $\theta_c$ is 38.7° in the case where the prism is made of ZnSe (refractive index=2.4) and the object has a refractive index=1.5. When the angle of incidence is smaller than the critical angle, it does not generate total reflection. The beam returns to the cassegrain mirror 120 by the usual reflection of the object 110.

Figure 4A:
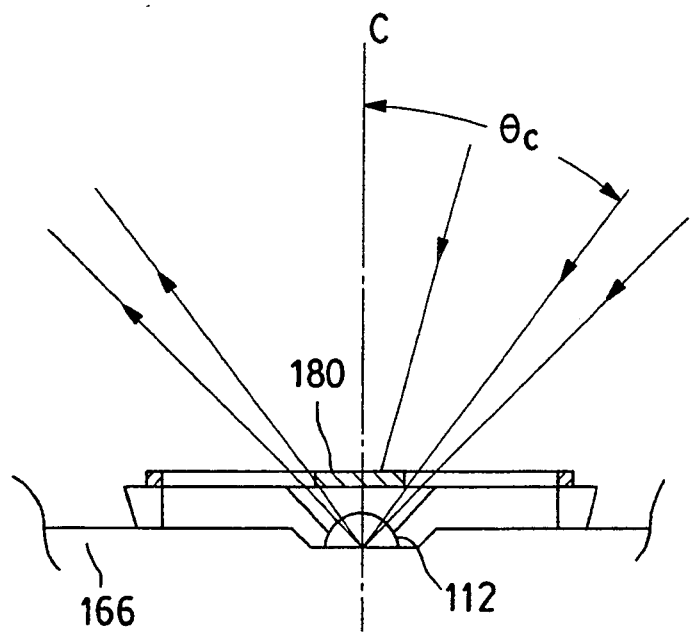
FIGS. 4A and 4B are an explanatory view of a mask which is used for the example shown in the FIG. 1.
Figure 4B:
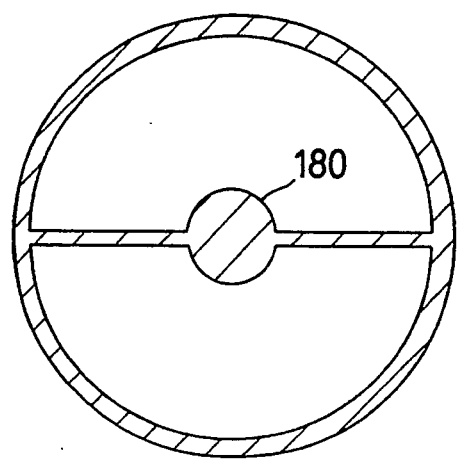

For preventing the contamination of the reflected light into the total reflected light, a mask as shown in FIG. 4 is preferably used.

The mask 180 is provided at the upper part of the prism 112 and removes a beam of light of which the angle of incidence is smaller than the critical angle. Although the critical angle is different according to the refractive index of an object, it is usual that an object having a refractive angle being about 1.5 is selected when using the ZnSe prism. Therefore, the mask size should be adjusted.

As described above, a one step cassegrain mirror is used in the example. However, it is possible to arrange more than one cassegrain mirror serially so as to correspond the central axes to each other and same one-way. As a result, it is possible to make a numerical aperture bigger as compared with the resolution. Therefore, the range of the measuring area is enlarged, total reflection measurement precision improves, and visual observation is easier.

According to the total reflection measuring apparatus of the present invention, a prism is positioned in the shadow part under the cassegrain secondary mirror when selecting the part to be measured. As a result, visual observation can provide very clear images.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. A total reflection measuring apparatus comprising a cassegrain mirror which has a cassegrain primary mirror and a cassegrain secondary mirror, and which focuses light which is reflected by the secondary mirror and the primary mirror on an object to be measured;

a prism positioned at a location behind said cassegrain secondary mirror; and a prism lifting means for lifting the prism between a shadow behind the cassegrain secondary mirror and the object to be measured.

2. A total reflection measuring apparatus according to claim 1, wherein said prism lifting means is provided with;

a cylinder, a moving shaft which is inserted in the cylinder wherein said shaft moves in the cylinder, a prism holding board which is fixed on the bottom of the moving shaft, and a spring which pulls the moving shaft toward the cassegrain secondary mirror.

3. A total reflection measuring apparatus according to claim 1, wherein said prism lifting means is provided with;

a stopper ring which positions the prism in contact with the object.

4. A total reflection measuring apparatus according to claim 1 further comprising a mask located between said secondary mirror and said prism.

* * * * *